United States Patent [19]

Seidel

[11] Patent Number: 4,883,910

[45] Date of Patent: Nov. 28, 1989

[54] OXIDATION OF ORGANICS BY A VANADIUM CONTAINING HETEROPOLYANION COMPOUND

[75] Inventor: William C. Seidel, Hockessin, Del.

[73] Assignee: E. I. Du Pont De Nemours and Company, Wilmington, Del.

[21] Appl. No.: 714,196

[22] Filed: Mar. 20, 1985

[51] Int. Cl.[4] .......................................... C07C 51/245
[52] U.S. Cl. ................... 562/528; 562/408; 562/418; 562/538; 562/543
[58] Field of Search ............... 562/528, 538, 543, 418, 562/408

[56] References Cited

U.S. PATENT DOCUMENTS 3,590,080 6/1971 Beesley et al. .................. 562/528

FOREIGN PATENT DOCUMENTS 2262657 9/1975 France .............................. 562/538

Primary Examiner—Werren B. Lone

[57] ABSTRACT

An organic compound having a cyclic aliphatic moiety is oxidized with a vanadium containing heteropolyanion compound having the formula $$A_m XY_{12-n} V_n^{+5} O_{40}$$

wherein
A is H, Li, K or Na:
X is $P^{+5}$, $Si^{+4}$, $Ge^{+4}$ or $B^{+3}$;
Y is Mo or W;
n is an integer from 1 to 10; and
m is $3+n$ where X is $P^{+5}$ or $As^{+5}$, $4+n$ where X is $Si^{+4}$ or $Ge^{+4}$, and $5+n$ where X is $B+3$.

No metal catalyst is required. Exemplary is the oxidation of cyclohexanone, cyclohexanol, or any combination thereof to obtain adipic acid.

17 Claims, No Drawings

OXIDATION OF ORGANICS BY A VANADIUM CONTAINING HETEROPOLYANION COMPOUND

FIELD OF THE INVENTION

This invention relates to a process for oxidation of an organic compound having a cyclic aliphatic moiety with a vanadium containing heteropolyanion compound.

BACKGROUND OF THE INVENTION

Pentavalent vanadium is the choice oxidant for the conversion of cyclic alcohols and ketones to dicarboxylic acids because of its high reactivity and selectivity.

Vanadium containing heteropolyacids (HPAs) have been used as oxidation catalysts in conjunction with palladium co-catalysts and in the presence of molecular oxygen. Kozhevnikov and Matveev, *Applied Catalysis,* 5:135–150 (1983), disclose the oxidation of sulfur compounds with catalytic amounts of a vanadium containing HPA in the presence of molecular oxygen. The reference discloses that HPAs of various composition are used as catalysts for the liquid-phase oxidation of tetralin and olefins. The authors disclose a two-component catalyst of Pd(II) and a vanadium containing HPA. The disclosed oxidation reactions are conducted at 20° to 125° C. in water, acetic acid and DMFA (dimethylformamide) in the presence of molecular oxygen. The reference also discloses that HPAs are effective catalysts for the epoxidation of olefins.

Kozhevnikov et al., Dokl. Akad. Nauk. SSSR 235 (6), 1347–1349 (1977), disclose the liquid phase oxidation of ethanol, 2-propanol, 1-butanol, and 2-butanol to carbonyl compounds with a two-component catalyst of Pd(II) and phosphomolybdovanadic HPA of the formula $H_{3+n}PMo_{12-n}V_nO_{40}$ (n=1–8). The disclosed oxidation reaction is conducted at 96°–125° C. and 6–36 atm. oxygen pressure.

Littler and Walters, *J. Chem. Soc.,* 4046–4052 (1959), disclose the oxidation of cyclohexanol to adipic acid in the presence of molecular oxygen with pentavalent vanadium at a concentration of 0.05M in sulfuric acid or perchloric acid. The authors disclose an oxidative mechanism for cyclohexanol involving the cation $[V(OH)_3]^{2+}$ in perchloric acid, and $[VO(H_2O)SO_4]^+$ or a similar complex ion in sulfuric acid. It is also suggested that the oxidation of cyclohexanone by acid vanadium involves $]V(OH)_3]^{2+}$ in perchloric acid and a sulfate complex in sulfuric solutions.

Marisic, *J. Am. Chem. Soc.,* 62: 2312–2317 (1940), disclose vapor phase partial oxidation of naphthalene with molecular oxygen over heteropolyacid catalysts, vanadium pentoxide, and molybdenum oxide. Fused vanadium pentoxide catalyst at 481° C. oxidized naphthalene to phthalic anhydride with a 79% yield.

SUMMARY OF THE INVENTION

This invention provides a process for liquid phase oxidation of an organic compound having a cyclic aliphatic moiety of at least 6 carbon atoms selected from the group consisting of olefins, alcohols, diols, and ketones. The process comprising contacting in aqueous media in the absence of molecular oxygen at a temperature from about 60°–150° C. the organic compound and at least one vanadium containing heteropolyanion compound having the formula $$A_mXY_{12-n}V_n^{+5}O_{40}$$

wherein
A is H, Li, K or Na;
X is $P^{+5}$, $As^{+5}$, $Si^{+4}$, $Ge^{+4}$ or $B^{+3}$;
Y is Mo or W;
n is an integer from 1 to 10; and
m is 3+n where X is $P^{+5}$ or $As^{+5}$, 4+n where X is $Si^{+4}$ or $Ge^{+4}$, and 5+n where X is $B^{+3}$.

Preferably, the cyclic aliphatic moiety is selected from the group consisting of ketones and alcohols. Most preferably, the organic compound is cyclohexanone, cyclohexanol, or any combination thereof.

DETAILED DESCRIPTION OF THE INVENTION

The present invention provides a process for liquid phase oxidation of an organic compound having a cyclic aliphatic moiety of at least 6 carbon atoms with at least one vanadium containing heteropolyanion compound. It has been found that incorporation of vanadium into a specified heteropolyanion structure produces a highly soluble form of pentavalent vanadium which remains highly reactive and selective. The high solubility allows for the use of pentavalent vanadium in stoichiometric amounts for the oxidation of organic compounds in the absence of oxygen and metal catalysts under conditions which would be considered commercially practical.

In the process of the present invention a vanadium containing heteropolyanion compound is mixed with an organic compound having a cyclic aliphatic moiety of at least 6 carbon atoms in an aqueous media to form a reaction mixture. Preferably, the aqueous media is water. The reaction mixture is heated in the absence of molecular oxygen at a temperature of from about 60° to 150° C. to effect the oxidation of the organic compound. Preferably, the reaction mixture is heated at a temperature of from about 100° to 110° C. Timing is not critical. Preferably, the reaction mixture is heated from about 30 to 260 minutes. The concentration of heteropolyanion in the reaction mixture is preferably from about 0.001 to 0.8M, based on the total volume of the reaction mixture. Most preferably, the concentration is from about 0.5 to 0.8M. The process of the present invention can be operated in a batch mode, continuous mode, or any combination thereof. The process of the invention can be conducted at atmospheric or elevated pressures.

Organic compounds suitable for oxidation in the process of the present invention have a cyclic aliphatic moiety of at least 6 carbon atoms selected from the group consisting of olefins, alcohols, diols, and ketones. Examples of suitable organic compounds include cyclohexanone, cycloheptanone, cyclooctanone, cyclododecanone, cyclohexanol, cycloheptanol, cyclooctanol, cyclododecanol, cyclohexene, cycloheptene, cyclooctene, cyclododecene, 1,2-cyclohexanediol, 1,2-cycloheptanediol, 1,2-cyclooctanediol, 1,2-cyclododecanediol, 2-hydroxycyclohexanone, 2-hydroxycycloheptanone, 2-hydroxycyclooctanone, and 2-hydroxycyclododecanone. These cyclic structures may also be part of a fused aromatic-aliphatic compound or a complex fused ring structure, like a steroid. A partial list of suitable fused aromatic-aliphatic compounds includes 2,3-benzo-1-oxocyclohexane, 2,3-benzo-1-oxocycloheptane, 3,4-benzo-1-oxocyclohexane, 3,4-benzo-1-oxocycloheptane, 3,4-benzo-1-hydroxycyclohexane, 3,4-benzo-1-hydroxycyclohexane, and 2,3-benzo-1-hydroxycycloheptane. Examples of suitable steroids include cholesterol, cholestanol, and pregnanedione. Preferably, the organic compound has a cyclic aliphatic moiety selected from the group consisting of ketones and alcohols. Preferably, the cyclic aliphatic moiety is of 6 to 12 carbon atoms. Most preferably, the organic compound is cyclohexanol, cyclohexanone, or any combination thereof.

The vanadium containing heteropolyanion compound used in the process of the present invention has the formula $$A_m XY_{12-n} V_n^{+5} O_{40}$$

wherein
A is H, Li, K or Na;
X is $P^{+5}$, $As^{+5}$, $Si^{+4}$, $Ge^{+4}$ or $B^{+3}$;
Y is Mo or W;
n is an integer from 1 to 10; and
m is $3+n$ where X is $P^{+5}$ or $As^{+5}$, $4+n$ where X is $Si^{+4}$ or $Ge^{+4}$, and $5+n$ where X is $B^{+3}$.

Preferably, moiety X is phosphorus and moiety Y is molybdenum. Preferably n is an integer from 1 to 3, most preferably 2. The heteropolyanion compound can be prepared according to a method generally corresponding to that disclosed by Tsigdinos and Hallada, *Inorg. Chem.*, 7: 437 (1968), which is incorporated herein by reference. As stated above, an advantage of the heteropolyanion compound of the present invention is that no metal catalyst is required to effect oxidation.

The heteropolyanion compound used in the process of the present invention possesses high solubility at temperatures of less than 150° C. The art discloses that solutions of $V_2O_5$ dissolved in sulfuric or perchloric acid oxidize cyclic alcohol and ketone to dicarboxylic acid. It has been found that these solutions exhibit low solubility of vanadium$^{+5}$ at low temperatures. A saturated solution of $V_2O_5$ in 0.5M $H_2SO_4$ at 175° C. has a vanadium $^{+5}$ concentration of 0.2M. Increased temperatures required to improve solubility result in a decreased yield of dicarboxylic acid. The heteropolyanion compound used in the process of the present invention exhibits improved solubility. A saturated solution of the heteropolyanion compound in water at 30° C. has a vanadium $^{+5}$ concentration of from about 0.8 to 2.4M.

The process of the present invention is further described by the following examples, wherein all parts and percentages are by weight and degrees are Celsius. Acid yields are based on the initial concentration of cyclic organic compound in a reaction mixture. Analysis of adipic acid was conducted by gas liquid phase chromatography (g.l.p.c.) of the methyl esters resulting from $BF_3/CH_3OH$ treatment of organic acids according to the following procedure.

PROCEDURE FOR ANALYSIS OF ADIPIC ACID

1–10 mL of reaction mixture are placed into a 50 mL round-bottom flask equipped with a heating mantle, reflux condenser, and magnetic stirrer. A solution of 8 mg pimelic acid in 5 mL methanol and 10 mL of 10% $BF_3/CH_3OH$ are added to the reaction mixture. The resulting combination is refluxed for 10 minutes, cooled to ambient temperature, and poured into a 125 mL separating funnel containing 50 mL of water. The water fraction is extracted with 3×20 mL portions of dichloromethane. The resulting extracts are combined and stirred with 2 g of sodium bicarbonate for one minute. The combined extracts are filtered through glass wool into a round-bottom flask and evaporated to 4 mL on a vacuum rotary evaporator to form samples.

The samples are analyzed on a Hewlett Packard 5840A gas chromatograph. 0.2 μL aliquots are applied to a 2.74 m×0.32 cm (9 ft×⅛ in) stainless steel column containing 10% high polarity cyanosilicone stationary phase sold by Supelco as "SP-2340" on a flux-calcined support sold by supelco as "Chrom WAW", 80/100 mesh, according to U.S. Standard Sieve Series. Column, detector, and injection temperatures are 160°, 250° and 250°, respectively, and a flame ionization detector is employed. Helium is injected into the column at a rate of 30 cc/min. Air and hydrogen are injected into the detector at rates of 250 cc/min and 30 cc/min, respectively. The concentration of adipic acid is determined relative to the pimelic acid as internal standard.

EXAMPLES 1–7

Oxidation of 2-Hydroxycyclohexanone 10 mL of a solution containing the specified heteropolyanion composition and 2-hydroxycyclohexanone in water were placed in a 50 mL round-bottom flask equipped with a magnetic stirrer, heater and reflux condenser. The concentration of the heteropolyanion in the solution was 0.02M. The solution was refluxed at 101° in the absence of molecular oxygen for a specified time, cooled to ambient temperature, and analyzed by g.l.p.c. for adipic acid. The results are presented in the table below.

TABLE

OXIDATION OF 2-HYDROXYCYCLOHEXANONE

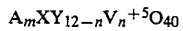

| Ex. | HPA(1) | | Time | Adipic Acid Yield |
|---|---|---|---|---|
| 1 | $H_4PMo_{11}VO_{40}$ | 0.005 M | 30 min | 85% |
| 2 | $H_5PMo_{10}V_2O_{40}$ | 0.005 M | 30 min | 90% |
| 3 | $H_6PMo_9V_3O_{40}$ | 0.005 M | 30 min | 84% |
| 4 | $H_5PMo_{10}V_2O_{40}$ | 0.010 M | 60 min | 91% |
| 5 | $H_6PMo_9V_3O_{40}$ | 0.015 M | 60 min | 87% |
| 6 | $H_5PW_{10}V_2O_{40}$ | 0.010 M | 60 min | 48% |
| 7 | $H_5PW_{10}V_2O_{40}$ | 0.005 M | 90 min | 80% |

EXAMPLE 8

Oxidation of Cyclohexanone with $H_5PMo_{10}V_2O_{40}$ 10 mL of 0.5M $H_5PMo_{10}V_2O_{40}$ in water were placed into a 14 mL polymer tube containing a small magnetic stirring bar. 64 μL (60.7 mg) of cyclohexanone were added with stirring to form a reaction mixture. The tube was purged with nitrogen, sealed with a torch, and heated in an oil bath at 100° for 2 hours. The tube was removed from the oil bath and cooled to ambient temperature. The reaction mixture was analyzed by g.l.p.c. for adipic acid and cyclohexanone. The yield of adipic acid was 85.0 mg (94.4%). There was no trace of cyclohexanone in the chromotograph.

EXAMPLE 9

Oxidation of Cyclohexanol with $H_5PMo_{10}V_2O_{40}$ 10 mL of 0.5M $H_5PMo_{10}V_2O_{40}$ in water were placed into a 14 mL polymer tube containing a small magnetic stirring bar. 40 μL (37.4 mg) of cyclohexanol were added with stirring to form a reaction mixture. The tube was purged with nitrogen, sealed with a torch and heated in an oil bath at 100° for 3 hours and 50 minutes. The tube was removed from the oil bath and cooled to ambient temperature. The reaction mixture was analyzed by g.l.p.c. for adipic acid and cyclohexanol. The yield of adipic acid was 20.7 mg (83%).

EXAMPLE 10

Oxidation of Cyclohexanol with $H_5PMo_{10}V_2O_{40}$ 12 mL of 0.83M $H_5PMo_{10}V_2O_{40}$ in water were placed into a 14 mL polymer tube containing a small magnetic stirring bar. 40 μL (37.4 mg) of cyclohexanol were added with stirring to form a reaction mixture. The tube was purged with nitrogen, sealed with a torch and heated in an oil bath at 100° for 4 hours and 20 minutes. The tube was removed from the oil bath and cooled to ambient temperature. The reaction mixture was analyzed by g.l.p.c. for adipic acid and cyclohexanol. The yield of adipic acid was 49.5 mg (91%). Only a trace of cyclohexanol was detected.

EXAMPLE 11

Oxidation of Cyclohexene with $H_5PMo_{10}V_2O_{40}$ 10 mL of 0.42M $H_5PMo_{10}V_2O_{40}$ in water were placed into a 14 mL polymer tube containing a small magnetic stirring bar. 50.6 mg (63 μL) of cyclohexene were added with stirring to form a reaction mixture. The tube was purged with nitrogen, sealed with a torch and heated in an oil bath at 146° for 3 hours. The tube was removed from the oil bath and cooled to ambient temperature. The reaction mixture was analyzed by g.l.p.c. for cyclohexene, cyclohexanol and adipic acid. The yield of adipic was 17.2 mg (44%). The analysis detected 2.5–5.0 mg cyclohexene and 24.4 mg cyclohexanol.

EXAMPLE 12

Oxidation of Cyclododecanone with $H_5PMo_{10}V_2O_{40}$ 10 mL of 0.455M $H_5PMo_{10}V_2O_{40}$ in water were placed into a 14 mL polymer tube containing a small magnetic stirring bar. 0.140 g of cyclododecanone were added with stirring to form a reaction mixture. The tube was purged with nitrogen, sealed with a torch and heated in an oil bath at 100° for 90 minutes. The tube was removed from the oil bath and cooled to ambient temperature. Crude 1,10-decanedicarboxylic acid was recovered from the reaction mixture by filtration, washed with distilled water, and air dried to give 0.1216 g of product. The aqueous phase of the reaction mixture was analyzed by g.l.p.c. and found to contain only 0.0044 g 1,10-decanedicarboxylic acid. The total yield of dodecanedioic acid was 0.126 g (71%).

EXAMPLE 13

Oxidation of Cycloheptanone with $H_5PMo_{10}V_2O_{40}$ 10 mL of 0.455M $H_5PMo_{10}V_2O_{40}$ in water were placed into a 14 mL polymer tube containing a small magnetic stirring bar. 85.6 mg (90 μL) of cycloheptanone were added with stirring to form a reaction mixture. The tube was purged with nitrogen, sealed with a torch and heated in an oil bath at 100° for one hour. The tube was removed from the oil bath and cooled to ambient temperature. The reaction mixture was analyzed by g.l.p.c. for cycloheptanone and pimelic acid. The yield of pimelic acid was 0.106 g (90%). Only a trace of cycloheptanone was detected.

EXAMPLE 14

Oxidation of Trans-1,2-Cyclohexanediol with $H_5PMo_{10}V_2O_{40}$ 25 mL of 0.5M $H_5PMo_{10}V_2O_{40}$ in water were placed into a 50 mL round-bottom flask equipped with a magnetic stirring bar, reflux condenser and heating mantle. 246 mg of trans-1,2-cyclohexanediol were added with stirring to form a reaction mixture. The reaction mixture was refluxed in the absence of molecular oxygen for 6 hours and 45 minutes. The mixture was cooled to ambient temperature and analyzed by g.l.p.c. for adipic acid. The yield of adipic acid was 146 mg (48%).

EXAMPLE 15

Oxidation of Cyclohexanone with $H_{10}PMo_5V_7O_{40}$ 100 mL of 0.16M $H_{10}PMo_5V_7O_{40}$ in water were mixed with 3 mL of concentrated $H_2SO_4$ to form a solution. The solution was charged to a 125 mL electrochemical oxidation reactor and heated to 100°. In the absence of molecular oxygen, cyclohexanone was pumped into the reactor at 0.005M/hour to form a reaction mixture. After two hours, the color of the reaction mixture changed from orange to green and the addition of cyclohexanone was stopped. The reaction mixture was analyzed by g.l.p.c. for adipic acid and cyclohexanone. The yield of adipic acid was 85% at 100% conversion of the cyclohexanone.

What is claimed is:

1. A process for liquid phase oxidation of (1) a cyclic aliphatic compound selected from the group consisting of olefins, alcohols and ketones, said cyclic aliphatic compound having at least 6 carbon atoms or (2) a 2,3- or 3,4-benzo-cycloaliphatic compound in which the cycloaliphatic moiety is an alcohol or ketone of 6 to 12 carbon atoms; said process comprising contacting in aqueous media in the absence of molecular oxygen at a temperature of from about 60° to 150° C. the cyclic aliphatic compound or the benzocycloaliphatic compound and at least one vanadium containing heteropolyanion compound having the formula $A_mXY_{12-n}V_n^{+5}O_{40}$ wherein A is H, Li, K or Na;
X is $P^{+5}$, $As^{+5}$, $Si^{+4}$, $Ge^{+4}$ or $B^{+3}$;
Y is Mo or W;
n is an integer from 1 to 10; and
m is 3+n where X is $P^{+5}$ or $As^{+5}$, 4+n where X is $Si^{+4}$ or $Ge^{+4}$ and 5+n where X is $B^{+3}$.

2. The process of claim 1 wherein the cyclic aliphatic compound is selected from the group consisting of alcohols and ketones.

3. The process of claim 1 wherein the cyclic aliphatic compound is of 6 to 12 carbon atoms.

4. The process of claim 3 wherein the cyclic aliphatic compound is selected from the group consisting of cyclohexene, cyclohexanone, cyclohexanol, cycloheptanone, cyclododecanone, cyclohexanediol, and a combination thereof.

5. The process of claim 4 wherein the cyclic aliphatic compound is cyclohexanone, cyclohexanol, or a combination thereof.

6. The process of claim 2 wherein A is H, X is $P^{+5}$, Y is Mo and n is an integer from 1 to 3.

7. The process of claim 6 wherein n is 2.

8. The process of claim 7 wherein the aqueous media is water.

9. The process of claim 8 wherein the oxidation is conducted at a temperature from about 100° to 110° C.

10. The process of claim 9 wherein the concentration of said heteropolyanion is about 0.001 to 0.8 molar.

11. The process of claim 10 wherein the concentration of said heteropolyanion is about 0.5 to 0.8 molar.

12. The process of claim 5 wherein A is H, X is $P^{+5}$, Y is Mo and n is an integer from 1 to 3.

13. The process of claim 12 wherein n is 2.

14. The process of claim 13 wherein the aqueous media is water.

15. The process of claim 14 wherein the oxidation is conducted at a temperature from about 100° to 110° C.

16. The process of claim 15 wherein the concentration of said heteropolyanion is about 0.001 to 0.8 molar.

17. The process of claim 16 wherein the concentration of said heteropolyanion is about 0.5 to 0.8 molar.

* * * * *